United States Patent [19]

Vargas

[11] Patent Number: 5,306,848
[45] Date of Patent: Apr. 26, 1994

[54] HYDROGENATION CATALYST FOR OXO ALCOHOL PROCESS

[75] Inventor: Jose M. Vargas, Baton Rouge, La.

[73] Assignee: Exxon Chemical Patents Inc., Linden, N.J.

[21] Appl. No.: 962,428

[22] Filed: Oct. 16, 1992

[51] Int. Cl.$^5$ .................... C07C 29/16; C07C 31/125; C07C 29/90
[52] U.S. Cl. .................................. 568/883; 568/881; 568/914; 502/220
[58] Field of Search .................. 568/883, 914, 881

[56] References Cited

U.S. PATENT DOCUMENTS

| | | | |
|---|---|---|---|
| 2,638,488 | 5/1953 | Cerveny | 568/914 |
| 2,728,798 | 12/1955 | Russum et al. | 568/914 |
| 4,443,638 | 4/1984 | Yates | 568/914 |
| 4,709,105 | 11/1987 | Grenacher et al. | 568/883 |
| 5,030,774 | 7/1991 | Oswald et al. | 568/882 |

FOREIGN PATENT DOCUMENTS 89304856.1  11/1989  European Pat. Off.

OTHER PUBLICATIONS

Kirk-Othmer, Encyclopedia of Chemical Technology, Third Edition, vol. 16, John Wiley & Sons, pp. 637-653, 1981, Oxo Process.

*Primary Examiner*—Joseph E. Evans
*Attorney, Agent, or Firm*—J. J. Mahon

[57] ABSTRACT

The hydrogenation steps and hydrofinishing steps of the cobalt catalyst oxo process for the preparation of alcohols by the hydroformylation of olefin are carried out using a trimetallic catalyst composed of metal oxides, particularly nickel oxide, molybdenum oxide and cobalt oxide supported on alumina or an alumina-silica in sulfided and non-sulfided form.

9 Claims, No Drawings

HYDROGENATION CATALYST FOR OXO ALCOHOL PROCESS

This invention relates to an improved process for preparing alcohols by the oxo process. More particularly this invention relates to an improvement in the hydrogenation step of the oxo process characterized in the use of certain trimetallic hydrogenation catalysts.

The oxo process is well known in the art and is generally described in detail in Kirk-Othmer, Encyclopedia of Chemical Technology, Volume 16, 3rd ed., John Wiley & Sons, pp. 637–653, 1981.

In the well known oxo process, olefins are hydroformylated by reaction with carbon monoxide and hydrogen, generally charged as synthesis gas (syn gas) mixtures, in the presence of a cobalt oxo catalyst in dissolved form to form a mixture of oxo aldehydes and alcohols. This oxo reaction is typically carried out at syn gas pressures of from about 10.33 MPa to 31.00 MPa (1500 to 4500 psig) and at temperatures of from about 65° C. to 230° C. Thereafter, the product mixture containing the alcohols and aldehydes is recovered and can then be treated by known means to hydrogenate the aldehydes to form additional quantities of the corresponding alcohols. These alcohols, in turn, are widely used as chemical intermediates in the manufacture of plasticizers, detergents, solvents and the like.

Prior to the hydrogenation step, the crude oxo reaction effluent, which contains dissolved cobalt catalysts, the aldehyde and alcohol products and reaction by-products together with any metallic contaminants, is generally treated to remove the dissolved cobalt catalyst, which then for reasons of economy must be recycled to the oxo reactor.

"Demetalled" hydroformylation reaction product or crude oxo alcohol product is the reaction product which is substantially depleted of the transition metal cobalt catalyst required for the hydroformylation reaction. Such crude oxo product will generally contain cobalt in an amount of from about 0.05 to 3.0 wt.%, calculated as elemental cobalt. The concentration of aldehyde in the crude oxo alcohol product is generally from about 40 to 75 wt.%.

The next step in the oxo process is the hydrogenation of the crude alcohol product which is typically carried out at pressures of about 20.67 MPa to 31.00 MPa (3000 to 4500 psig) using sulfided bimetallic cobalt and molybdenum oxides or nickel and molybdenum oxide supported on alumina as the hydrogenation catalyst. Because of the high content of carbonyl-containing compounds present in the crude alcohol product the use of relatively high pressures with the traditional bimetallic catalysts has been required in order to achieve the desired yield of alcohol product.

The use of bimetallic catalysts in the hydrogenation of crude alcohol oxo product is disclosed, for example, U.S. Pat. No. 5,030,774, issued Jul. 9, 1991 and European Application 89304856.1, published Nov. 29, 1989. The present invention is based on the discovery that certain trimetallic catalysts are useful in the two separate hydrogenation steps practiced in the cobalt catalyzed oxo process.

In accordance with the present invention there has been discovered an improvement in the process for preparing oxo alcohols by the cobalt catalyzed hydroformylation of olefins which comprises the sequential steps of (a) hydroformylation of $C_5$–$C_{12}$ olefins by reaction with carbon monoxide and hydrogen in the presence of a cobalt hydroformylation catalyst (hydrido cobalt carbonyl), (b) demetalling the crude reaction product of step (a) to recover therefrom homogeneous cobalt catalyst and to separate therefrom essentially cobalt-free crude alcohol product which contains 20 wt.% of more of carbonyl-containing compounds such as aldehydes, acetals, ethers and esters, (c) hydrogenating the crude alcohol product of step (b) at elevated temperatures and pressures to reduce the carbonyl-containing compounds to alcohols, (d) distilling the product of step (c) and recovery therefrom oxo alcohols containing very small proportions of carbonyl compounds, and (e) hydrofinishing (by hydrogenation) the product of step (d) to provide a substantially pure alcohol product, the improvement being characterized in that step (c) or step (e) or both may be carried out using a supported trimetallic catalyst consisting of nickel, cobalt and molybdenum.

The olefin feedstock for the hydroformylation reaction is typically a commercial olefin feedstock which may include linear and branched $C_2$–$C_{17}$ monoolefins. Preferably, the olefin feedstock contains a significant amount of a branched $C_5$–$C_{12}$ monoolefin. The preferred olefins include amylenes from petroleum cracking, heptenes, octenes, nonenes and dodecenes from fractionation of oligomers of $C_3$–$C_4$ olefin, and octenes from dimerization and codimerization of isobutylene and 1- and 2-butenes.

Cobalt catalyzed hydroformylation is typically carried out at a pressure of 15–30 MPa and a temperature of about 120°–190° C. Cobalt catalyst is present in its active form as hydrido cobalt carbonyl in a concentration of from 0.05–3.0 wt.%, preferably 0.05 to wt.%, calculated as metal based on olefin feedstock. The synthesis gas typically has a $H_2$:CO volume ratio in the range of 0.9:1 to 1.5:1.

After separation of the cobalt catalyst from the crude reaction product the crude alcohol product, which is hydrogenated in accordance with this invention, will contain a substantial proportion of carbonyl-containing compounds which are produced as a result of the hydroformylation reaction. These carbonyl-containing compounds mainly include aldehydes, acetals, formates, esters and ethers, and the crude alcohol product will contain 20 wt% or more, more typically 40 to 60 wt%, of aldehydes and other carbonyl compounds which are to be hydrogenated to the desired alcohol product.

The catalysts useful in the process of the invention are trimetallic nickel, cobalt and molybdenum catalysts in the form of oxides of those metals and supported on either alumina or silica alumina. Preferred catalysts are those composed of 1.0 wt % nickel oxide, 4.5 wt % cobalt oxide and 16.0 wt % molybdenum oxide, 77.3 wt % alumina and 1.2 wt % silica, or composed of 0.7 wt % nickel oxide, 3.8 wt % cobalt oxide, 17.0 wt % molybdenum oxide, 69.6 wt % alumina and 8.9 wt % silica.

These catalysts are also particularly preferred for use in their sulfided form after being sulfided by the techniques well known in the art using gaseous ($H_2S$) or liquid sulfiding compounds, such as dimethyl sulfide or dimethyl disulfide solutions, to convert the oxides of the metals to their corresponding sulfides. Typically about 80% to 100% of the oxides are converted to metal sulfides in such a sulfiding procedure.

The catalysts of the present invention may be used either in the first hydrogenation step of the oxo process or in the final hydrofinishing (hydrogenation) step, or in both. When used in the first hydrogenation step, the advantage results in enabling this step to be carried out at relatively lower pressures, i.e., less than 10.34 MPa (1500 psig) while still achieving a desired conversion of carbonyl-containing compounds to the alcohol product. When used as the catalyst in the final hydrofinishing step, which is also a hydrogenation reaction, its advantage is that the carbonyl number (mg KOH/g) can be effectively reduced to levels less than 0.2 mg KOH/g in the finished alcohol product. It has been found that use of the trimetallic catalysts of the invention in the hydrofinishing step provide the desired carbonyl numbers at superior conversion rates when compared with bimetallic catalysts. The hydrofinishing step is preferably carried out at about 5.51 MPa (800 psig) and 130° C. (266° F.), this step effects trace removal of carbonyl species by hydrogenation.

The invention is illustrated by the following examples which are not to be considered as limitative of its scope.

EXAMPLE 1

This example demonstrates the use of the trimetallic catalysts in the hydrogenation of a crude oxo alcohol product, referred to as step (c) above. The hydrogenation was carried out at 6.89 MPa (1000 psig) over a temperature range of 160° C. (320° F.) to 198.9° C. (390° F.), and alcohol yield improved with temperature.

Two 316 stainless steel, ½" diameter reactors with appropriate high pressure connectors were each charged with 65 cubic centimeters of catalyst material to be evaluated. The catalyst loaded reactors are immersed in a fluid-bed, constant temperature sand-bath equipped with electrical heaters for temperature control. Appropriate mechanical connections were installed to allow reactor operation at nominal pressure of 6.89 MPa (1000 psig) and nominal test temperatures from 160° C. (320° F.) to 198.9° C. (390° F.).

Under steady state conditions liquid feed and gaseous high purity hydrogen (>99 vol% H2) are pumped over the fixed catalyst bed. Liquid and gaseous product is subsequently depressurized and sampled periodically. Aliquots of liquid product and liquid feed are analyzed for composition by gas chromatography.

The liquid feed consists of demetalled hydroformylation product of crude aldehyde. Evaluations on the following feed types were performed: heptanal, nonanal, decanal; mixed with water at nominal water/feed of 3 vol %. Typical crude aldehyde feed component distribution appears in Table 1, below.

TABLE 1

| | Crude Aldehyde Feed Composition | | | |
|---|---|---|---|---|
| (1) Feed Type | (2) Lights, wt % (Olefin + Paraffin) | (3) Aldehyde + Formate Esters, wt % | (4) Alcohol, wt % | (5) Heavier than Alcohol, wt % |
| H-1, Heptanal-1 | 1.07 | 60.59 | 20.47 | 17.87 |
| H-2, Heptanal-2 | 1.19 | 61.27 | 20.23 | 17.31 |
| H-3, Heptanal-3 | 1.16 | 63.00 | 20.47 | 15.37 |
| H-4, Heptanal-4 | 1.43 | 63.96 | 20.29 | 14.32 |
| N, Nonanal | 8.06 | 69.69 | 9.16 | 13.09 |
| N-1, Nonanal-1 | 8.24 | 78.33 | 4.75 | 8.68 |
| N-2, Nonanal-2 | 8.15 | 77.29 | 3.13 | 11.43 |
| N-3, Nonanal-3 | 7.51 | 82.13 | 3.27 | 7.09 |

TABLE 1-continued

| | Crude Aldehyde Feed Composition | | | |
|---|---|---|---|---|
| (1) Feed Type | (2) Lights, wt % (Olefin + Paraffin) | (3) Aldehyde + Formate Esters, wt % | (4) Alcohol, wt % | (5) Heavier than Alcohol, wt % |
| D, Decanal | 15.81 | 27.88 | 22.00 | 34.31 |

A trimetallic catalyst was evaluated. The catalyst properties prior to sulfiding appear in Table 2, below.

TABLE 2

| Trimetallic Catalyst Properties | |
|---|---|
| Chemical Composition | |
| Component | wt % |
| MoO3 | 17 |
| NiO | 0.7 |
| CoO | 4 |
| Balance: Al2O3 and SiO2 | |
| Physical Properties | |
| Surface Area: | 290 m2/g |
| Total Pore Volume: | 0.5 ml/g |
| Bulk density: | 0.60 g/ml |

The catalyst was sulfided by treatment with a gaseous sulfiding agent comprising 10 vol.% H2S in H2 at (390° F.) 199° C. for a 2 hour period, thereafter the temperature was increased to 339.4° C. (643° F.) and maintained at that temperature for 12 hours.

The catalyst described in Table 2 was tested at conditions listed in Table 3. Product composition for different test samples included in Table 3 was determined by gas chromatography.

Comparing product aldehyde composition in Table 3 (column (4)) with corresponding feed aldehyde content in Table 1 (column (3)) for the three crude aldehyde feed types tested, aldehyde conversion in excess of 95 wt % is attained. The high level of aldehyde conversion is obtained at equally high selectivity to the desired alcohol product (Table 3, column (5)).

EXAMPLES 1A and 1B

Comparative Evaluation Against Co/Mo and Ni/Mo Alumina Supported Sulfided Catalysts

EXAMPLE 1A

This example demonstrates the advantage of trimetallic catalysts over bimetallic Ni/Mo (Cat-B, per description in Table 2a) and bimetallic Co/Mo (Cat-A, per description in Table 2a) in the hydrogenation of crude oxo alcohol product, referred to as step (c) above. The hydrogenation was carried out at 6.89 MPa (1000 psig) at 198.9° C. (390° F.). Undesired byproduct formation was reduced, thus obtaining improvement in alcohol yield, when using trimetallic catalyst (Test # 39E014, Table 3), relative to byproduct formation obtained under equivalent test conditions (Test # 51E001) with bimetallic Ni/Mo (Cat-B) catalyst and bimetallic Co/Mo (Cat-A) catalyst (Test # 88C003, Table 3a).

Test conditions were similar to those described in Example 1 above. Typical crude aldehyde feed component distribution appears in Table 1.

The catalysts described in Table 2a were tested at conditions listed in Table 3a. Product composition for different test samples included in Table 3a was determined by gas chromatography.

A first comparison is presented where alcohol is produced through catalytic hydrogenation of nonanal feed. Comparing bimetallic catalyst product aldehyde composition in Table 3a, (column (6), Tests # 51E001 and 88C003) with trimetallic catalyst product aldehyde composition in Table 3 (column (4), Test 39E014), aldehyde conversion in excess of 95 wt % is attained. However, higher product alcohol content is obtained with trimetallic catalyst (Table 3, column (5), Test # 39E014) than that obtained with bimetallic catalysts (Table 3a, column (7), Test 51E001 and 88C003). The improved alcohol yield obtained with trimetallic catalyst results from reduced increment in Light (Table 3, column (7), Test # 39E014) and Heavy (Table 3, column (8), Test # 39E014) product composition. Higher levels of Light (Table 3a, column (9), Tests # 51E001 and 88C003) and Heavy (Table 3a, column (10), Tests # 51E001 and 88C003) product composition are obtained with bimetallic catalyst.

Similar to the nonanal case described above, a second case where alcohol is catalytically produced from heptanal feed is presented next. Bimetallic product aldehyde composition (Table 3a, column (6), Tests # 43E009 and 43E008) and trimetallic product aldehyde composition (Table 3, column (4), Tests 39E0;7 and 39E018) indicates aldehyde conversion in excess of 95 wt%. However better aldehyde utilization is obtained with trimetallic catalyst, particularly at higher temperature (198.9° C. (390° F.)) as indicated by the lower Heavy product content (Table 3, column (8), Test 39E017) relative to the corresponding, but slightly higher Heavy product content (Table 3a, column (10), Test # 43E009) obtained with bimetallic Ni/Mo (Cat-B) catalyst. Of greater significant advantage is the reduced Light product composition (Table 3, column (7), Test 39E017) obtained with trimetallic catalyst relative to the higher Light product composition (Table 3a, column (9), Test # 43E009) obtained with bimetallic Ni/Mo (Cat-B) catalyst.

EXAMPLE 1B

This example demonstrates the advantage of trimetallic catalyst performance at lower pressure relative to equivalent bimetallic catalyst performance at higher pressure. Hydrogenation tests were carried out at 6.89 MPa (1000 psig) for trimetallic catalyst and at 20.67 MPa (3000 psig) for bimetallic Co/Mo (Cat-A, per description in Table 2a).

Test conditions were similar to those described in Example above. Typical crude aldehyde feed component distribution appears in Table 1.

The bimetallic Co/Mo (Cat-A) catalyst described in Table 2a was tested at elevated pressure conditions (20.67 MPa (3000 psig)) listed in Table 3a. Product composition for different test samples included in Table 3a was determined by gas chromatography.

In this example, elevated pressure (20.67 MPa (3000 psig)) results obtained with bimetallic Co/Mo catalyst (Table 3a, Test 88C007) will be compared against trimetallic catalyst at corresponding lower pressure operation (6.89 MPa (1000 psig)) in Table 3 (Test # 39E014).

Superior aldehyde conversion is obtained with trimetallic catalyst at 1000 psig relative to bimetallic Co/Mo at 3000 psig. The case is illustrated by the lower product aldehyde composition (0.58 wt%) attained with trimetallic catalyst (Table 3, column (4), Test # 39E014) at 6.89 MPa (1000 psig) relative to a higher product aldehyde content produced with bimetallic Co/Mo (Table 3a, column (6), Test # 88C007) at 3000 psig. The Co/Mo bimetallic produced even higher (i.e. inferior, lower aldehyde conversion) product aldehyde content (1.23 wt%) at 6.89 MPa (1000 psig), demonstrated in Table 3a, Test # 88C003.

TABLE 2a

Representative Reference Bimetallic Catalyst Properties (For Aldehyde Hydrogenation Reference Examples)

| Catalyst Type | Chemical Composition Component wt % (a) | | | Physical Properties | | |
|---|---|---|---|---|---|---|
| | $MoO_3$ | NiO | CoO | Surface Area, $m^2/g$ | Total Pore Volume, ml/g | Bulk Density, g/ml |
| Cat-A | 15.4 | 0 | 4.4 | 142 | 0.53 | 0.71 |
| Cat-B | 20.0 | 4.0 | 0 | 180 | 0.45 | 0.82 |

(a) - Balance Chemical Composition: $Al_2O_3$ and $SiO_2$

TABLE 3

Summarized Trimetallic Catalyst Hydrogenation Test Conditions and Results
All tests conducted at 6.89 MPa (1000 psig), nominal Feed Rate of 130 ml/hr,
Water Rate of 4 ml/hr, Linear Hourly Space Velocity of 1 ml catalyst per (ml feed/hr).

| Test Conditions | | Product Composition | | | | Undesired Yield | |
|---|---|---|---|---|---|---|---|
| (1) Test # Feed Type | (2) Temp, °C. | (3) Lights, wt % | (4) Aldehyde + Formate, wt % | (5) Alcohol, wt % | (6) Heavier than Alcohol, wt % | (7) Delta Lights (a), wt % | (8) Delta Heavier than Alcohol (b), wt % |
| 39E014 N | 198.9 | 9.08 | 0.58 | 69.73 | 20.61 | 1.02 | 7.52 |
| 39E016 D | 198.9 | 15.91 | 0.20 | 72.98 | 10.91 | 0.10 | −23.40 |
| 39E017 H-1 | 198.9 | 2.07 | 0.68 | 81.98 | 15.27 | 1.00 | −2.60 |
| 39E018 H-2 | 160.0 | 0.98 | 1.65 | 86.62 | 10.75 | −.21 | −6.36 |

(a) - Calculated as: {[Product Lights Composition, Column (3) in Table 3] − [Feed Lights Composition, Column (2) in Table 1]}

(b) - Calculated as: {[Product Heavy Composition, Column (6) in Table 3] − [Feed Heavy Composition, Column (5) in Table 1]}

TABLE 3a

Summarized Hydrogenation Test Conditions and Results (a)
(For Aldehyde Hydrogenation Reference Examples)

| | Test Conditions | | | | Product Composition | | | | Undesired Yield | |
|---|---|---|---|---|---|---|---|---|---|---|
| | (1) | (2) | (3) | (4) | (5) | (6) | (7) | (8) | (9) | (10) |
| | Cat. | Feed | Temp, | Press, | Lights, | Ald + Form, | Alc | Heavier than Alcohol | Delta Lights (b), | Delta Heavier than Alcohol (c), |
| Test # | Type | Type | °C. | psig | wt % | wt % | wt % | wt % | wt % | wt % |
| 51E001 | Cat-B | N-1 | 198.9 | 1000 | 16.53 | 0.64 | 62.46 | 20.37 | 8.29 | 11.68 |
| 88C003 | Cat-A | N-2 | 198.9 | 1000 | 8.00 | 1.23 | 57.06 | 33.70 | −0.15 | 22.26 |
| 88C007 | Cat-A | N-3 | 198.9 | 3000 | 7.35 | 0.79 | 80.04 | 11.82 | −0.16 | 4.74 |
| 43E009 | Cat-B | H-3 | 198.9 | 1000 | 4.53 | 0.73 | 81.34 | 13.40 | 3.37 | −1.97 |
| 43E008 | Cat-B | H-4 | 160.0 | 1000 | 1.81 | 0.66 | 89.28 | 8.25 | 0.38 | −6.07 |

(a) - All tests at nominal Feed Rate of 130 ml/hr, Water Rate of 4 ml/hr, Linear Hourly Space Velocity (LHSV) of 1 ml catalyst/(ml feed/hr)
(b) - Calculated as: {[Product Lights Composition, Column (5) in Table 3a] − [Feed Lights Composition, column (2) in Table (1)]}
(c) - Calculated as: {[Product Heavy Composition, Column (8) in Table 3a] − [Feed Heavy Composition, Column (5) in Table (1)]}

EXAMPLE 2

This example demonstrates the use of the trimetallic catalyst in the hydrofinishing step of the oxo process.

Two (2) 316 stainless steel, ½" diameter reactors with appropriate high pressure connectors are each charged with 65 cubic centimeters of catalyst to be tested and connected in series (130 cc total effective catalyst volume). The catalyst loaded reactors are immersed in a fluid-bed sand bath equipped with electrical heaters for adequate temperature control. Appropriate mechanical connections are installed to allow reactor operation at nominal pressure of 5.51 MPa (800 psig) and nominal temperature of 130° C. (266° F.).

Under steady state conditions liquid feed (distilled isodecanol and water, at 0 to 2.0 vol.% water/alcohol) and gaseous high purity hydrogen (>99 vol.% $H_2$) are pumped up-flow over the fixed catalyst beds. Liquid product is depressurized and sampled periodically. Aliquots of liquid product are analyzed for carbonyl content.

Thus, hydrofinishing activity is evaluated based on carbonyl reduction attained over different catalysts at equivalent residence time, temperature and pressure.

EXAMPLE 2A

A reference case is considered, using existing art to catalytically hydrofinish isodecanol. The bimetallic catalyst used for comparison in Ni/Mo on alumina. Catalyst composition and physical properties are included in Table Catalyst performance is indicated in Table 5.

EXAMPLE 2B

A trimetallic catalyst, Ni/Co/Mo on alumina was used to catalytically hydrofinish isodecanol. Nominal catalyst composition and physical properties are included in Table 4. Catalyst performance is indicated in Table 5.

EXAMPLE 2C

A second trimetallic catalyst, Ni/Co/Mo on alumina was used to catalytically hydrofine isodecanol. Nominal catalyst composition and physical properties are included in Table 4. Catalyst performance is indicated in Table 5.

TABLE 4

Typical Catalyst Chemical and Physical Properties

| Catalyst Type | Metal Oxide Content, wt % | | | Support Oxide Content wt % | | Surface Area $m^2/g$ | Pore Volume cc/g | Pore Diameter Angstroms |
|---|---|---|---|---|---|---|---|---|
| | Ni | Co | Mo | Al | Si | | | |
| Ex. 2A | 4.0 | — | 19.5 | 76.5 | — | 190 | 0.40 | 85 |
| Ex. 2B | 0.7 | 3.8 | 17.0 | 69.6 | 8.9 | 285 | 0.46 | 65 |
| Ex. 2C | 1.0 | 4.5 | 16.0 | 77.3 | 1.2 | 260 | 0.47 | 72 |

The results are shown in Table 5 below. Both of the trimetallic catalysts used in Example 2B and 2C show a superior catalyst effectiveness when compared with the bimetallic catalyst of Example 2A. The trimetallic catalysts achieve the desired carbonyl number for the finished alcohol product at a residence time substantially less than that for the bimetallic catalyst.

TABLE 5

Catalyst Hydrofinishing Performance Comparison

| Catalyst Type | Residence Time (t, hr) to Attain 0.1 mg KOH/g (2) | Catalyst Effectiveness Improvement, % (1) |
|---|---|---|
| Ex. 2A | 0.72 ($t_{Base}$) | Base |
| Ex. 2B | 0.48 | 50 |
| Ex. 2C | 0.25 | 188 |

(1) Catalyst Effectiveness defined as:
$$\frac{(t_{Base} - t)}{t} \times 100$$
(2) Carbonyl number of finished alcohol

What is claimed is:

1. In the process for preparing oxo alcohols by the cobalt catalyzed hydroformylation of olefins, which process comprises the sequential steps of
   (a) hydroformylation of olefins by reaction with carbon monoxide and hydrogen in the presence of a cobalt hydroformylation catalyst to produce a crude reaction product;
   (b) demetalling the crude product of step (a) to recover therefrom homogeneous cobalt catalyst and separate therefrom crude alcohol product, the crude alcohol product containing 20 wt. % or more of carbonyl compounds;
   (c) hydrogenating the crude alcohol product at an elevated temperature and pressure to reduce the carbonyl compounds to alcohols;

(d) distilling the product of step (c) and recovery therefrom alcohol products containing very small proportions of carbonyl compounds; and (e) hydrofinishing the product to step (d) to provide a substantially pure alcohol product, the improvement which comprises conducting step (c) or (e), or both, in the presence of a catalyst being a supported trimetallic nickel, cobalt and molybdenum catalyst.

2. The process of claim 1 wherein the catalyst support is silica-alumina or alumina.

3. The process of claim 1 or 2 wherein the catalyst is sulfided.

4. The process of claim 1 wherein the trimetallic catalyst is in the form of oxides of nickel, cobalt and molybdenum.

5. The process of claim 4 wherein the catalyst comprises about 0.7 wt. % nickel oxide, about 3.8 wt. % cobalt oxide and about 17.0 wt. % molybdenum oxide.

6. The process of claim 4 wherein the catalyst comprises about 1.0 wt. % nickel oxide, about 4.5 wt. % cobalt oxide and about 16.0 wt. % molybdenum oxide.

7. The process of claim 5 or claim 6 wherein the catalyst is sulfided.

8. The process of claim 1 or claim 4 wherein the trimetallic catalysts is used and step (e) is carried out at a pressure of about 5.51 MPa (800 psig) and a temperature of about 130° C. (266° F.).

9. The process of claim 1 or claim 4 wherein the trimetallic catalyst is used and step (c) is carried out at a pressure below 10.34 MPa (1500 psig).

* * * * *